United States Patent
Lee et al.

(10) Patent No.: US 11,319,294 B2
(45) Date of Patent: May 3, 2022

(54) METHOD FOR MANUFACTURING CALTERIDOL

(71) Applicant: ENZYCHEM LIFESCIENCES CORPORATION, Chungcheongbuk-do (KR)

(72) Inventors: Jong Soo Lee, Gangwon-do (KR); Dae Myoung Yun, Gangwon-do (JP); Byuong Woo Lee, Chungcheongbuk-do (KR)

(73) Assignee: ENZYCHEM LIFESCIENCES CORPORATION, Chungcheongbuk-Do (KR)

( * ) Notice: Subject to any disclaimer, the term of this patent is extended or adjusted under 35 U.S.C. 154(b) by 0 days.

(21) Appl. No.: 17/193,129

(22) Filed: Mar. 5, 2021

(65) Prior Publication Data
US 2021/0284614 A1 Sep. 16, 2021

(30) Foreign Application Priority Data
Mar. 11, 2020 (KR) .................. 10-2020-0030266

(51) Int. Cl.
*C07D 257/02* (2006.01)
(52) U.S. Cl.
CPC ........ *C07D 257/02* (2013.01); *C07B 2200/13* (2013.01)
(58) Field of Classification Search
CPC .................................................. C07D 257/02
USPC ........................................................ 540/474
See application file for complete search history.

(56) References Cited

U.S. PATENT DOCUMENTS

| 6,166,201 A | 12/2000 | Ripa et al. | |
| 10,793,532 B2 * | 10/2020 | Platzek | C07D 257/02 |

FOREIGN PATENT DOCUMENTS

| CN | 110835326 A * | 2/2020 | ........... C07D 257/02 |
| CN | 110835326 A | 2/2020 | |
| KR | 10-2019-0088793 A | 7/2019 | |
| WO | 98/56776 A1 | 12/1998 | |
| WO | WO-9856776 A1 * | 12/1998 | ........... C07D 257/02 |
| WO | 2019/143074 A1 | 7/2019 | |
| WO | WO-2019143074 A1 * | 7/2019 | ............. A61K 49/06 |

OTHER PUBLICATIONS

Office Action dated Mar. 26, 2021 issued in corresponding Korean Application No. 10-200-0030266.
Extended Search Report dated May 19, 2021 issued in corresponding European Application No. 21160976.3.

* cited by examiner

*Primary Examiner* — D Margaret M Seaman
(74) *Attorney, Agent, or Firm* — Nath, Goldberg & Meyer; Joshua B. Goldberg; Tanya E. Harkins

(57) ABSTRACT

It is disclosed a method for preparing calteridol used as MRI contrast agents. It provides a method for preparing calteridol comprising: obtaining teridol represented by the following Formula 2 by reacting gadoteridol represented by the following Formula 1 with decomplexing agent; and obtaining calteridol represented by the following Formula 3 by reacting calcium ion with teridol represented by following Formula 2.

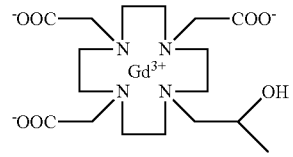

[Formula 1]

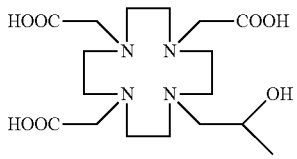

[Formula 2]

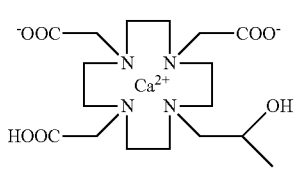

[Formula 3]

6 Claims, No Drawings

METHOD FOR MANUFACTURING CALTERIDOL

CROSS-REFERENCE TO RELATED APPLICATION

This application claims benefit of priority to Korean Patent Application No. 10-2020-0030266 filed on Mar. 11, 2020, the entire content of which is incorporated herein by reference.

FIELD OF THE DISCLOSURE

The present invention relates to a method for preparing calteridol, and more particularly, to a method for preparing calteridol used in MRI contrast agents.

BACKGROUND

Gadoteridol is marketed all over the world under the brand name ProHance® in the field of gadolinium-containing contrast agents.

In the case of gadolinium-containing contrast agents, an excess of complex-forming ligand is applied in the form of a calcium complex to prevent the release of trace amounts of free gadolinium. This can solve the safety problem for Nephrogenic Systemic Fibrosis caused by the toxicity of gadolinium cations.

According to the following Scheme 1 disclosed in Example 7 of international patent WO9856776A1, 1,4,7,10-tetraazacyclododecane-1,4,7-triacetic acid (hereinafter, DO3A) is prepared and reacted with propylene oxide to prepare 10-(2-hydroxypropyl)-1,4,7,10-tetraazacyclododecane-1,4,7-triacetic acid (hereinafter, teridol). Then, a method of preparing 10-(2-hydroxypropyl)-1,4,7,10-tetraazacyclododecane-1,4,7-triacetate calcium salt (hereinafter, calteridol) by adding calcium carbonate is disclosed.

[Scheme 1]

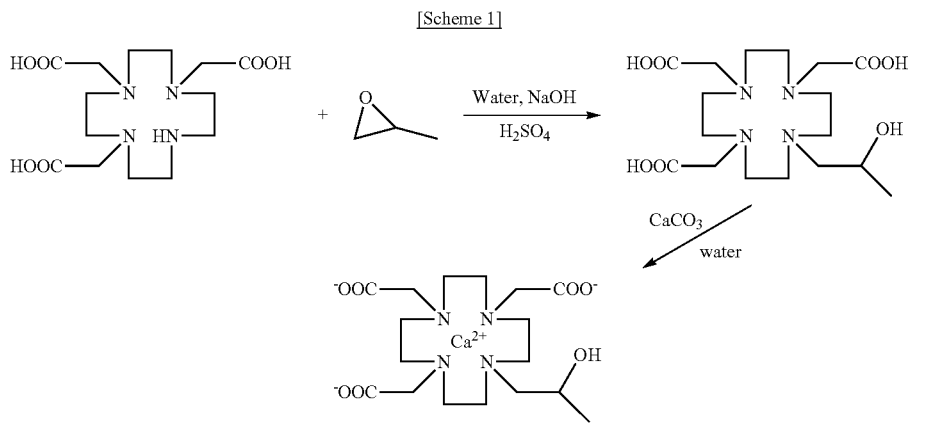

However, it is difficult to obtain high purity DO3A in this method, and there is a disadvantage that a further process for removing it by using propylene oxide in the last step.

Therefore, it is required to develop a method for preparing high purity calteridol through an economical and simplified process.

SUMMARY OF THE INVENTION

Technical Objects

Accordingly, an object of the present invention is to provide a method for preparing calteridol with high purity, simple process, and economical using a gadoteridol intermediate (teridol).

Another object of the present invention is to provide a method for preparing calteridol in an economical and simpler than the method for preparing calteridol using the conventional known DO3A as a starting material.

Technical Solution

In order to achieve the above object, the present invention provides a method for preparing calteridol comprising: obtaining a teridol represented by the following Formula 2 by reacting gadoteridol represented by the following Formula 1 with decomplexing agent; and obtaining a calteridol represented by the following Formula 3 by reacting calcium ion with teridol represented by following Formula 2.

[Formula 1]

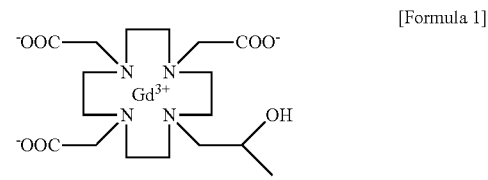

[Formula 2]

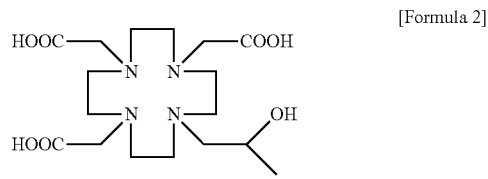

[Formula 3]

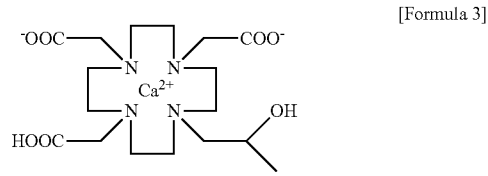

Effects of the Invention

As described above, the method for preparing calteridol according to the present invention is simpler than the method for preparing calteridol using the conventional known DO3A as a starting material, and the calteridol can be manufactured economically.

DETAILED DESCRIPTION OF THE PREFERRED EMBODIMENTS

Hereinafter, the present invention will be described in more detail.

The present invention discloses a method for preparing calteridol, as shown in Scheme 2 below, for preparing calteridol using gadoteridol as a starting material. The gadolinium is removed from the gadoteridol using an organic acid and an ion exchange resin, and impurities are removed using a nanofilter to obtain high purity teridol. Wherein calcium carbonate is used to provide calcium ion and it crystallizes to prepare high purity calteridol.

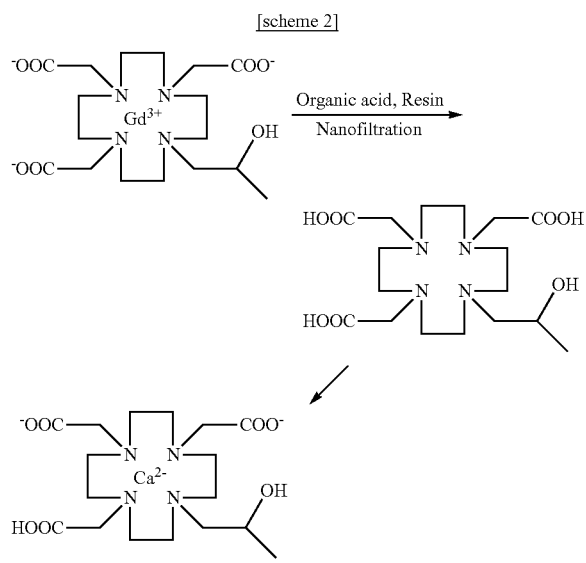

[scheme 2]

Specifically, in order to prepare calteridol according to the present invention, first, 2, 2', 2"-[10-(2-hydroxypropyl)-1,4,7,10-tetraazacyclododecane-1,4,7-triyl]triacetate gadolinium complex (hereinafter, Gadoteridol) represented by the following Formula 1 as a starting material, and a decomplexing agent are reacted to obtain 2, 2', 2"-[10-(2-hydroxypropyl)-1,4,7,10-tetraazacyclododecane-1,4,7-triyl] triacetic acid (hereinafter, butrol) represented by the following Formula 2.

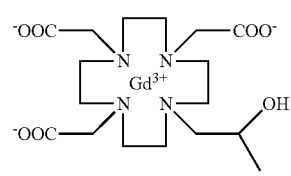

[Formula 1]

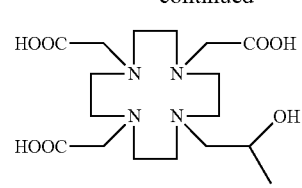

[Formula 2]

The decomplexing agent decomplexes the gadolinium of gadoteridol to form a gadolinium salt that is poorly soluble in water, so that teridol can be isolated through a filtration process. The decomplexing agent may be used tartaric acid, succinic acid, citric acid, fumaric acid, malic acid, oxalic acid, and the like, and tartaric acid is preferably used. The amount of decomplexing agent used is 2.0 to 6.0 equivalents, preferably 3.0 to 4.0 equivalents, based on (with respect to) 1.0 equivalent of gadoteridol. If the amount of the decomplexing agent is small, the reactivity may be reduced, and the reaction time may take a long time, or the yield may decrease. Also, quality problems may occur due to the generation of flexible materials. If the amount of the decomplexing agent is large, since the unreacted decomplexing agent must be removed after the reaction is completed, the process becomes complicated and additional cost may be incurred.

The reaction uses purified water, and the reaction temperature is 80 to 90° C. According to the reaction temperature, problems of quality and cost increase may occur. The reaction time is 1 to 2 hours. If the reaction time is too short, unreacted products and quality problems may occur, and if the reaction time is too long, an additional cost according to an increase in working time may occur.

The reactant may be purified and separated by a method such as an ion exchange resin, thereby obtaining teridol from which gadolinium was removed. The ion exchange resin may be used by passing the cation and anion resin in serial order. The reaction product including the salt generated from the reaction is filtered again, so that remaining decomplexing agent and by-products can be removed. The purified filtrate is concentrated, so that teridol having a purity of 90% or more can be obtained.

Specifically, it is filtered using a nanofilter. The nanofilter system may separate and purify inorganic materials having a salt and other molecular weight through an organic layer, as a reverse osmosis device designed to filter or concentrate substances having a molar mass of 200 to 300 Dalton or more in the spiral type of an organic layer.

The teridol represented by Formula 2 and calcium ion are reacted and crystallized to obtain 2,2',2"-[10-(2-hydroxypropyl)-1,4,7,10-tetraazacyclododecane-1,4,7-triyl] triacetate calcium complex (hereinafter, calteridol) represented by Formula 3.

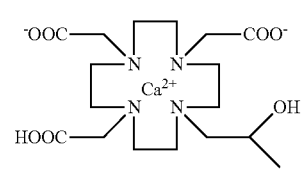

[Formula 3]

The reactant uses purified water, and the source of calcium ion may be used calcium carbonate, calcium hydroxide, calcium chloride, and the like, and calcium carbonate is preferably used.

The calteridol according to the present invention may further include calteridol in which the equivalent ratio of teridol and calcium ion is 1:1, as well as calteridol calcium form in which the equivalent ratio of teridol and calcium ion is 2:3. The calteridol calcium is a form produced when calcium ion are further included than calteridol.

Specifically, the amount of the calcium ion source used is 0.8 to 2.5 equivalents, preferably 0.9 to 1.8 equivalents, based on 1.0 equivalent of teridol. More specifically, the calcium ion may include calteridol in which the content of the calcium ion is 0.9 to 1.1 equivalents with respect to the teridol, and the calteridol calcium in which the content of calcium ion is 1.5 to 1.8 equivalents, based on the teridol. Wherein, if the equivalent amount of the calcium source is too small, the complex is formed less, resulting in a decrease in yield, and if the amount is too large, there is a problem that the remaining calcium carbonate is not well filtered. And when the content of calcium ion exceeds 1.5 equivalents, calteridol calcium with a ratio of teridol and calcium of 2:3 is produced.

The reaction is generally carried out at a temperature of 80 to 90° C. If the temperature is too low, there is a decrease in the yield by a unreacted products, and if the temperature is too high, a problem may occur in the quality of the product. In addition, the reaction time of the teridol and calcium ion is 1 hour to 2 hours. If the reaction time is short, problems may occur yield reduction and crystallization by unreacted products, and if too long, problems may occur in quality such as generation of related substances.

After the reaction product is concentrated, it can be dissolved in purified water and crystallized and isolated with acetone. A crystallization solvent may be used organic solvents such as methanol, ethanol, isopropanol, and acetone, and acetone may be used preferably. Specifically, the mother liquor may be crystallized in purified water-acetone conditions generally at 45 to 55° C. The crystallized mixture is dried to obtain calteridol.

Hereinafter, the present invention will be described in more detail through examples, but the present invention is not limited by the following examples.

Example 1: Preparation of Teridol Represented by Formula 2

2,2',2"-[10-(2-hydroxypropyl)-1,4,7,10-tetraazacyclodo-decane-1,4,7-triyl] triacetate calcium complex (hereinafter, calteridol) (200.0 g), tartaric acid (102.1 g), and purified water (600 ml) were added to the reactor and the temperature was raised to 90° C. to proceed the reaction. After completion of the reaction, it was cooled to 20° C., and filtered. The filtrate is purified by passing through the positive and negative ions resin in serial order. The purified filtrate was carried out a nano-filter and concentrated under decompressed pressure to 2,2',2"-[10-(2-hydroxypropyl)-1,4,7,10-tetraazacyclododecane-1,4,7-Triyl]triacetic acid (teridol) 132.52 g (yield 91.5%) was obtained.

Example 2: Preparation of Calteridol Represented by Formula 3

2,2',2"-[10-(2-hydroxypropyl)-1,4,7,10-tetraazacyclodo-decane-1,4,7-Triyl]triacetic acid (teridol) (132.52 g), calcium carbonate (32.81 g), and purified water (530 ml) were added to the reactor. Then, the temperature was raised to 75° C., and stirred for 3 hours. After completion of the reaction, it was cooled to 10° C. and filtered. The filtered filtrate was concentrated, and then purified water (265 ml) was added. The temperature was raised to 40° C. and added to acetone (135 ml). When crystals are formed, the resulting crystals are cooled to 20° C. and filtered. It was dried to obtain 2,2',2"-[10-(2-hydroxypropyl)-1,4,7,10-tetraazacyclodo-decane-1,4,7-triyl]triacetate calcium complex (hereinafter, calteridol) 137.62 g (yield 91.0%).

The invention claimed is:

1. A method for preparing calteridol comprising:
obtaining teridol represented by the following Formula 2 by reacting gadoteridol represented by the following Formula 1 with a decomplexing agent of tartaric acid; and

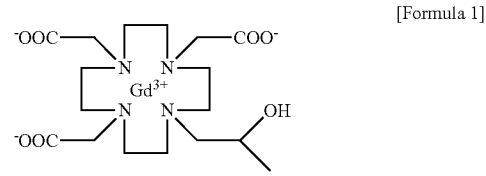

[Formula 1]

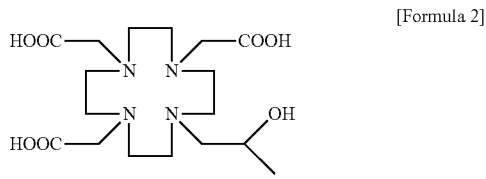

[Formula 2]

purifying and separating a reactant of the above step of obtaining teridol with an ion exchange resin, thereby obtaining teridol from which gadolinium was removed;
filtering and purifying the teridol using a nanofilter so that remaining decomplexing agent and by-products can be removed; and
obtaining calteridol represented by the following Formula 3 by reacting calcium ion with teridol represented by Formula 2

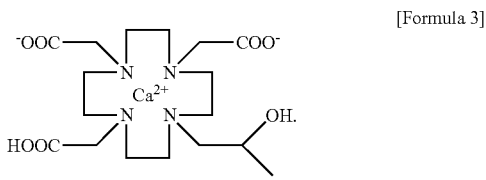

[Formula 3]

2. The method of claim 1, wherein the content of decomplexing agent is 2.0 to 6.0 equivalents, based on the gadoteridol.

3. The method of claim 1, wherein the calcium ion is selected from the group consisting of calcium carbonate, calcium hydroxide, calcium chloride, and mixtures thereof.

4. The method of claim 1, wherein the content of calcium ion is 0.9 to 1.1 equivalents based on the teridol, and an equivalent ratio of calcium ion and teridol is 1:1 in the calteridol.

5. The method of claim 1, wherein the content of calcium ion is 1.5 to 1.8 equivalents based on the teridol, and an equivalent ratio of calcium ion and teridol is 2:3 in the calteridol.

6. The method of claim 1, wherein the calteridol is crystallized from methanol, ethanol, isopropanol, or acetone.

* * * * *